United States Patent [19]
Ghirotto et al.

[11] Patent Number: 5,571,704
[45] Date of Patent: Nov. 5, 1996

[54] PROCESS FOR THE PREPARATION OF INTERMEDIATES USEFUL FOR THE SYNTHESIS OF BENZOTHIAZEPINES

[75] Inventors: Luca Ghirotto, Tortona; Stefano Servi; Claudio Fuganti, both of Milan; Angelo Gentile, Cernusco Sul Naviglio; Claudio Giordano, Monza, all of Italy

[73] Assignee: Zambon Group S.p.A., Vicenza, Italy

[21] Appl. No.: 404,284

[22] Filed: Mar. 14, 1995

Related U.S. Application Data

[62] Division of Ser. No. 197,544, Feb. 17, 1994, which is a continuation of Ser. No. 698,853, May 13, 1991.

[30] Foreign Application Priority Data

May 17, 1990 [IT] Italy ......................................... 20348/90

[51] Int. Cl.$^6$ .............................. C12P 17/02; C12N 9/18; C12N 9/20
[52] U.S. Cl. .......................... 435/123; 435/135; 435/280; 435/197; 435/198
[58] Field of Search .................................... 435/123, 280, 435/135, 197, 198

[56] References Cited

U.S. PATENT DOCUMENTS

| | | | |
|---|---|---|---|
| 4,985,366 | 1/1991 | Bianchi et al. | 435/280 |
| 5,108,916 | 4/1992 | Cobbs et al. | 435/135 |
| 5,169,779 | 12/1992 | Zard et al. | 435/280 |
| 5,198,557 | 3/1993 | Giordano et al. | 549/513 |
| 5,204,248 | 4/1993 | Shibatani et al. | 435/119 |
| 5,244,803 | 9/1993 | Mori et al. | 435/123 |
| 5,407,828 | 4/1995 | Kierkels et al. | 435/280 |

FOREIGN PATENT DOCUMENTS

| | | |
|---|---|---|
| 0343714 | 11/1989 | European Pat. Off. . |
| 362550 | 4/1990 | European Pat. Off. . |
| 0362556 | 4/1990 | European Pat. Off. . |
| 0407033 | 1/1991 | European Pat. Off. . |

OTHER PUBLICATIONS

Vogel "Practical Organic Chemistry"(1957) pp. 122–136.
Cambou, Bernard, et al, Biotechnology and Bioengineering, vol. 26, No. 12, Dec. 1984, pp. 1449–1454, "Comparison of Different Strategies for the Lipase-Catalyzed Preparative Resolution of Racemic Acids and Alcohols: Asymmetric Hydrolysis Esterification, and Transesterification".

*Primary Examiner*—Herbert J. Lilling
*Attorney, Agent, or Firm*—Watson Cole Stevens Davis P.L.L.C.

[57] ABSTRACT

A process for the preparation of the compounds of formula

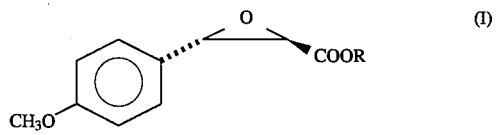

(wherein R has the meanings reported in the specification) by enzymatic transesterification of enantiomeric mixtures is described.

These compounds are intermediates useful in the synthesis of Diltiazem.

8 Claims, No Drawings

PROCESS FOR THE PREPARATION OF INTERMEDIATES USEFUL FOR THE SYNTHESIS OF BENZOTHIAZEPINES

This application is a division of application Ser. No. 08/197,544, filed Feb. 17, 1994, which in turn is a continuation of application Ser. No. 07/698,853, filed May 13, 1991.

The present invention relates to a process for the preparation of esters of (2R,3S)-3-(4-methoxyphenyl)-glycidic acid and particularly it relates to a process for the preparation of esters of (2R,3S)-3-(4-methoxyphenyl)-glycidic acid by enzymatic transesterification of enantiomeric mixtures.

The esters of (2R,3S)-3-(4-methoxyphenyl)-glycidic acid or (2R,3S)-2,3-epoxy-3-(4-methoxyphenyl)-propionic acid are intermediates useful for the synthesis of compound (+)-(2S,3S)-3-acetyloxy-5-[2-(dimethylamino)-ethyl]-2,3-dihydro-2-(4-methoxyphenyl)-1,5-benzothiazepin-4(5H)-one, a drug with coronary vasodilating activity known with the name of Diltiazem (Merck Index, XI Ed., No. 3188, page 505).

The preparation of Diltiazem, starting from esters of 3-(4-methoxyphenyl)-glycidic acid, can be carried out according to several methods in the literature.

Examples are reported in the British patent No. 1,236,467, in European patents No. 127882 and No. 158340 and in British patent application No. 2,167,063, all in the name of Tanabe Seiyaku Co. Ltd. In order to prepare Diltiazem is necessary to carry out an optical resolution.

It is clear to the man skilled in the art that it is economically more convenient to carry out a resolution step at an early stage of the process since the economic value of the product on which the resolution is carried out is lower and consequently the undesired iosmer has a lower cost.

Therefore, it is advantageous to have the esters of 3-(4-methoxyphenyl)-glycidic acid in an enantiomerically pure form since such compounds are the first optically active intermediates of the synthesis.

Several methods for the preparation of esters of 3-(4-methoxyphenyl)-glycidic acid in enantiomerically pure form are known.

Most of these methods foresee the resolution of a racemic mixture of 3-(4-methoxyphenyl)-glycidic acid with optically active bases and the subsequent esterification of the optically active acid (Japanese patent application No. 61/145160 in the name of Nippon Chemiphar Co. Ltd.: C. A. 106:32600u).

However, the difficult industrial application of such resolution methods is known. In fact, it is necessary to carry out the separation, the isolation and the purification of the diastereoisomeric salts under controlled conditions and there is the need of recovering the generally quite expensive optically active base.

Moreover, in the specific case, there is the problem of the high instability of 3-(4-methoxyphenyl)-glycidic acid which can cause serious troubles during the various steps of the resolution process. Enzymatic resolutions of esters of various structure are generally known (Angew. Chem. Int. Ed. Engl., 24, 617, 1985 and 28, 695, 1989).

However, as far as we know, enantioselective enzymatic transesterifications of esters of 3-(4-methoxyphenyl)-glycidic acid or of its analogous have never been described.

We have now found and it is the object of the present invention a process for the preparation of esters of (2R,3S)-3-(4-methoxyphenyl)-glycidic acid of formula

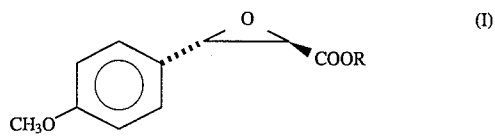

wherein R is a linear or branched $C_1$–$C_8$ alkyl group; a $C_5$–$C_6$ cycloalkyl group or a 2,2-dimethyl-1,3-dioxolane-4-methyl group; which consists in subjecting to enantioselective enzymatic transesterification a mixture of (2R,3S)-3-(4-methoxyphenyl)-glycidic acid methyl ester or ethyl ester (I, R=$CH_3$, $C_2H_5$) and its (2S,3R)-enantiomer (ent-I), by using an alcohol which is different from the alcohol esterifying compound I and ent-I and which is selected among a linear or branched $C_2$–$C_8$ aliphatic alcohol, a $C_5$–$C_6$ cycloaliphatic alcohol or 2,2-dimethyl-1,3-dioxolane-4-methanol, optionally in the presence of a suitable solvent or mixture of solvents, and in the separation of the transesterified ester from the untransesterified one.

The process object of the present invention allows to prepare intermediates useful for the synthesis of compounds with coronary vasodilating activity.

The enzymes useful for the transesterification reaction can be of different nature.

In particular, lipases of animal or microbial origin or proteolytic enzymes such as for example α-chymotrypsin can be used.

Among the lipases of animal origin useful in the process of the present invention, pig liver and pig pancreas lipases may be cited. Among the lipases of microbial origin, lipases from *Candida, Mucor, Pseudomonas* and *Aspergillus* microorganisms may be cited.

Examples of suitable alcohols are ethanol, n-propanol, 2-propanol, n-butanol, 2-butanol, 2-methyl-2-propanol, n-pentanol, 2-pentanol, 3-pentanol, n-hexanol, n-heptanol, 2-heptanol, n-octanol, 2-octanol, cyclohexanol, cyclopentanol and 2,2-dimethyl-1,3-dioxolane-4-methanol.

In particular n-butanol, 2-butanol, cyclohexanol, n-octanol and 2,2-dimethyl-1,3-dioxolane-4-methanol are the preferred alcohols. The lipases and the proteolytic enzymes act on enantiomerically opposite substrates.

In particular, in the enantiomeric mixture of compound I and ent-I (R=methyl, ethyl) the pancreatic enzyme, α-chymotrypsin, transesterifies the ester with the desired (2R, 3S)configuration, that is compound I, while the lipase transesterifies the (2S,3R)-enantiomer, that is compound ent-I.

The selection of the transesterifying agent (alcohol) to be used depends on the nature of R (methyl or ethyl) in the starting enantiomeric mixture.

In fact, according to the process object of the present invention, only one enantiomer transesterifies while the other remains unchanged.

Consequently, in order to separate the transesterified ester from the untransesterified at the end of the transesterification reaction, when R=methyl, all the above listed alcohols can be used, while when R=ethyl all the higher homologous of ethanol can be used. The transesterification reaction is carried out by contacting the enantiomeric mixture of compound I and ent-I (R=methyl, ethyl) with the enzyme and with the suitable alcohol.

Alternatively, the enzyme can be immobilized on suitable supports according to conventional techniques.

Examples of suitable supports are absorbent resins, acrylate polymers, porous materials, agarose or celite.

Preferably, a further suitable solvent or mixture of solvents such as for example hexane, cyclohexane, toluene, benzene, methyl ethyl ketone, diethyl ether is used if the transesterification reaction is carried out with the lipase enzyme.

At the end of the transesterification reaction, the two esters are separated according to known techniques.

For example, crystallization, chromatography or extraction with a suitable solvent or mixture of solvents may be used.

Examples of suitable solvents for the extraction are hexane or its mixtures with ethyl acetate, methanol and acetonitrile.

The operative conditions of the transesterification reaction are those normally used during the enzymatic reactions.

Such conditions take into account the pH and the temperature range in which each enzyme performs.

Generally such ranges are comprised between 6–11 pH units and between 0° C. and 70° C. respectively.

Preferably, the process of the present invention is carried out at a pH comprised between 6 and 8 and at a temperature comprised between 20° and 60° C.

At the end of the process the enzymes retain most of their activity and consequently they can be used again for several cycles.

Preferably, due to the easy availability on the market at lower cost, lipases of microbial origin and, in particular, lipases from *Candida Cylindracea* or α-chymotrypsin are used in the process object of the present invention.

The process object of the present invention allows to prepare the compounds of formula I with good yields and high enantiomeric purity and to recover also the undesired enantiomer.

It is possible, therefore, to carry out its racemization or inversion of configuration in order to increase the global yields of the process.

Moreover, the used enzyme retains its enzymatic activity and, consequently, it can be used again for several times.

If desired, compound I can be further purified by crystallization. As regard such feature, we have surprisingly found that when the compounds of formula I have at least about 80:20 enantiomeric ratio, their crystallization provides compounds I with a higher enantiomeric purity and this is independent from the source of the mixture. In particular, starting from the compounds of formula I with about 80:20 enantiomeric ratio, a 95:5 enantiomeric ratio is obtained by a simple crystallization.

Solvents suitable for the crystallization are lower alcohol such as for example methanol, ethanol, propanol, butanol.

Therefore, it is a further object of the present invention a process for increasing the enantiomeric purity of esters of (2R,3S)-3-(4-methoxyphenyl)-glycidic acid having at least an 80:20 enantiomeric ratio, which consists in crystallizing such esters with a suitable solvent.

In order to better illustrate the present invention without, however limiting it the following examples are now given.

EXAMPLE 1

Transesterification of racemic methyl ester of trans-3-(4-methoxyphenyl)-glycidic acid with lipase from *Candida Cylindracea* and n-butanol Racemic methyl ester of trans-3-(4-methoxyphenyl)-glycidic acid (10 g) was dissolved in a mixture constituted by hexane (250 ml) and n-butanol (60 ml).

To this solution lipase from *Candida Cylindracea* (SIGMA Chemical Co. Ltd.; TYPE VII) (30 g) was added.

The suspension was left at 25° C. for 26 hours under magnetic stirring.

At the end the lipase was filtered and the solvent was evaporated at reduced pressure.

An oil (10 g) was obtained which at the HPLC analysis (Chiracell OD column, 250 mm, internal diameter 4.6 mm, 10 μm, Daicel Chemical Industries Ltd.) showed to be constituted by methyl ester of trans-3-(4-methoxyphenyl)-glycidic acid (4.94 g) with an enantiomeric ratio (2R,3S):(2S,3R)=72:28 and by butyl ester of trans-3-(4-methoxyphenyl)-glycidic acid (3.49 g) with an enantiomeric ratio (2R,3S):(2S,3R)=22:78.

The thus obtained mixture constituted by methyl and butyl ester was separated by chromatography on silica gel (eluent hexane:ethyl acetate=7:3).

Methyl ester of trans-3-(4-methoxyphenyl)-glycidic acid (4.3 g) with an enantiomeric ratio (2R,3S):(2S,3R)=72:28 and butyl ester of trans-3-(4-methoxyphenyl)-glycidic acid (3.1 g) with an enantiomeric ratio (2R,3S):(2S,3R)=22:78 were thus obtained.

EXAMPLE 2

Transesterification of racemic methyl ester of trans-3-(4-methoxyphenyl)-glycidic acid with lipase from *Candida Cylindracea* and n-butanol The reaction was carried out in a similar way to that described in example 1 but by using the following amounts and conditions:

racemic methyl ester of trans-3-(4-methoxyphenyl)-glycidic acid (2 g)

lipase from *Candida Cylindracea* (AMANO Pharm. Co. Ltd.) (4.6 g)

hexane (46 ml)

n-butanol (9 ml)

temperature 27° C.

After about 4.5 hours the thus obtained mixture at the HPLC analysis showed to be constituted by methyl ester of trans-3-(4-methoxyphenyl)-glycidic acid (43%) with an enantiomeric ratio (2R,3S):(2S,3R)=89:11 and by butyl ester of trans-3-(4-methoxyphenyl)-glycidic acid (57%) with an enantiomeric ratio (2R,3S):(2S,3R)=21:79.

EXAMPLE 3

Transesterification of racemic methyl ester of trans-3-(4-methoxyphenyl)-glycidic acid with lipase from *Candida Cylindracea* and n-butanol The reaction was carried out in a similar way to that described in example 1 but by using the following amounts and conditions:

racemic methyl ester of trans-3-(4-methoxyphenyl)-glycidic acid (0.2 g)

lipase from *Candida Cylindracea* (AMANO Pharm. Co. Ltd.) (0.46 g)

hexane (0.9 ml)

n-butanol (0.9 ml)

temperature 32° C.

After about 3.5 hours the thus obtained mixture at the HPLC analysis showed to contain a mixture of methyl ester of trans-3-(4-methoxyphenyl)-glycidic acid (50%) with an enantiomeric ratio (2R,3S):(2S,3R)=72:28 and butyl ester of trans-3-(4-methoxyphenyl)-glycidic acid (50%) with an enantiomeric ratio (2R,3S):(2S,3R)=30.6:69.4.

EXAMPLE 4

Transesterification of racemic methyl ester of trans-3-(4-methoxyphenyl)-glycidic acid with lipase from *Candida*

Cylindracea and n-butanol

The reaction was carried out in a similar way to that described in example 3 but by using cyclohexane (4.6 ml), instead of hexane. After about 3 hours, the thus obtained mixture at the HPLC analysis showed to be constituted by methyl ester of trans-3-(4-methoxyphenyl)-glycidic acid (42.3%) with an enantiomeric ratio (2R,3S):(2S,3R)= 83.3:16.7 and by butyl ester of trans-3-(4-methoxyphenyl)-glycidic acid (57.7%) with an enantiomeric ratio (2R,3S):(2S,3R)=24.7:75.3.

EXAMPLE 5

Transesterification of racemic methyl ester of trans-3-(4-methoxyphenyl)-glycidic acid with lipase from *Candida Cylindracea* and cyclohexanol The reaction was carried out in a similar way to that described in example 1 but by using the following substances and conditions:

racemic methyl ester of trans-3-(4-methoxyphenyl)-glycidic acid (0.2 g)

lipase from *Candida Cylindracea* (AMANO Pharm. Co. Ltd.) (0.46 g)

hexane (4.6 ml)

cyclohexanol (0.9 ml)

temperature 32° C.

After about 4.5 hours the thus obtained mixture at the HPLC analysis showed to have an 85% titer and to be constituted by methyl ester of trans-3-(4-methoxyphenyl)-glycidic acid (48.6%) with an enantiomeric ratio (2R,3S):(2S,3R)=87.2:12.8 and by cyclohexyl ester of trans-3-(4-methylphenyl)-glycidic acid (51.4%).

The methyl and cyclohexyl esters were separated by column chromatography on silica gel and the methyl ester (2R,3S):(2S,3R)=87:13 was crystallized from ethanol to yield the enantiomerically pure methyl ester of (2R,3S)-3-(4-methoxyphenyl)-glycidic acid (enantiomeric excess higher than 99%).

EXAMPLE 6

Transesterification of racemic methyl ester of trans-3-(4-methoxyphenyl)-glycidic acid with lipase from *Candida Cylindracea* and (±)2-butanol The reaction was carried out in a similar way to that described in example 5 but by using (±)2-butanol (0.9 ml), instead of cyclohexanol.

After about 9 hours the thus obtained mixture at the HPLC analysis showed to have a 79% titer and to be constituted by methyl ester of trans-3-(4-methoxyphenyl)-glycidic acid (62.4%) with an enantiomeric ratio (2R,3S):(2S,3R)=77:23 and by 2-butyl ester of trans-3-(4-methoxyphenyl)-glycidic acid (37.6%).

EXAMPLE 7

Transesterification of racemic methyl ester of trans-3-(4-methoxyphenyl)-glycidic acid with lipase from *Candida Cylindracea* and (±)2-butanol The reaction was carried out in a similar way to that described in example 1 but by using the following substances and conditions:

racemic methyl ester of trans-3-(4-methoxyphenyl)-glycidic acid (2 g)

lipase from *Candida Cylindracea* (AMANO Pharm. Co. Ltd.) (2 g)

cyclohexane (25 ml)

(±)2-butanol (15 ml)

temperature 40° C.

After about 12 hours the thus obtained mixture at the HPLC analysis showed to have an 80% titer and to be constituted by methyl ester of trans-3-(4-methoxyphenyl)-glycidic acid (70%) with an enantiomeric ratio (2R,3S):(2S,3R)=67.6:32.4 and by 2-butyl ester of trans-3-(4-methylphenyl)-glycidic acid (30%).

EXAMPLE 8

Transesterification of racemic methyl ester of trans-3-(4-methoxyphenyl)-glycidic acid with lipase from *Candida Cylindracea* and (±)2-butanol in a column A chromatographic column (internal diameter 2 cm) was filled with a mixture constituted by lipase from *Candida Cylindracea* (AMANO Pharm. Co. Ltd.) (10 g) and celite (12.6 g).

The column was eluted with a solution of (±)2-butanol in cyclohexane (200 ml) (30:200 volumetric ratio) under slight pressure of nitrogen.

A solution of racemic methyl ester of trans-3-(4-methoxyphenyl)-glycidic acid (2 g) in a mixture (±)2-butanol:cyclohexane (30:200 volumetric ratio; 230 ml) was percolated into the column, always under slight pressure of nitrogen.

The eluate was re-charged for 7 times on the column.

At the end, the thus obtained mixture was analyzed by HPLC according to what described in example 1.

90% titer

Methyl ester of trans-3-(4-methoxyphenyl)-glycidic acid (70%) with an enantiomeric ratio (2R,3S):(2S,3R)= 69.7:30.3

2-butyl ester of trans-3-(4-methoxyphenyl)-glycidic acid (30%).

EXAMPLE 9

Transesterification of racemic methyl ester of trans-3-(4-methoxyphenyl)-glycidic acid with lipase from *Candida Cylindracea* and n-octanol The reaction was carried out in a similar way to that described in example 1 but by using the following substances and conditions:

racemic methyl ester of trans-3-(4-methoxyphenyl)-glycidic acid (1 g)

lipase from *Candida Cylindracea* (SIGMA Chemical Co. Ltd.; TYPE VII) (3 g)

hexane (40 ml)

methylethylketone (6 ml)

n-octanol (5 ml)

temperature 24° C.

After about 30 minutes the thus obtained mixture at the HPLC analysis showed to be constituted by methyl ester of trans-3-(4-methoxyphenyl)-glycidic acid (61.1%) with an enantiomeric ratio (2R,3S):(2S,3R)=72:28 and by octyl ester of trans-3-(4-methoxyphenyl)-glycidic acid (38.9%) with an enantiomeric ratio (2R,3S):(2S,3R)=19.8:80.2.

EXAMPLE 10

Transesterification of racemic methyl ester of trans-3-(4-methoxyphenyl)-glycidic acid with lipase from *Candida Cylindracea* and 2,2-dimethyl-1,3-dioxolane-4-methanol The reaction was carried out in a similar way to that described in example 1 but by using the following substances and conditions:

racemic methyl ester of trans-3-(4-methoxyphenyl)-glycidic acid (0.2 g)
lipase from *Candida Cylindracea* (0.46 g)
hexane (2 ml)
ethyl ether (2 ml)
2,2-dimethyl-1,3-dioxolane-4-methanol (1 ml)
temperature 26° C.

After about 13.5 hours the thus obtained mixture at the HPLC analysis showed to be constituted by methyl ester of trans-3-(4-methoxyphenyl)-glycidic acid (76.9%) with an enantiomeric ratio (2R,3S):(2S,3R)=61.5:38.5 and by 2,2-dimethyl-1,3-dioxolane-4-methyl ester of trans-3-(4-methoxyphenyl)-glycidic acid (23.1%).

EXAMPLE 11

Transesterification of racemic methyl ester of trans-3-(4-methoxyphenyl)-glycidic acid with lipase from *Candida Cylindracea* and 2,2-dimethyl-1,3-dioxolane-4-methanol The reaction was carried out in a similar way to that described in example 1 but by using the following substances and conditions:

racemic methyl ester of trans-3-(4-methoxyphenyl)-glycidic acid (0.2 g)
lipase from *Candida Cylindracea* (0.46 g)
cyclohexane (4 ml)
2,2-dimethyl-1,3-dioxolane-4-methanol (1.5 ml)
temperature 33° C.

After about 9.5 hours the thus obtained mixture at the HPLC analysis showed to be constituted by methyl ester of trans-3-(4-methoxyphenyl)-glycidic acid (54.4%) with an enantiomeric ratio (2R,3S):(2S,3R)=72.9:27.1 and by 2,2-dimethyl-1,3-dioxolane-4-methyl ester of trans-3-(4-methoxyphenyl)-glycidic acid (45.6%).

EXAMPLE 12

Transesterification of racemic methyl ester of trans-3-(4-methoxyphenyl)-glycidic acid with α-chymotrypsin and n-butanol Racemic methyl ester of trans-3-(4-methoxyphenyl)-glycidic acid (10 g) was dissolved in n-butanol (200 ml).

To this solution pH 7.4 phosphate buffer (410 ml) constituted by a 0.1M sodium hydroxide solution and by a 0.2M monopotassium phosphate solution was added.

To the thus obtained solution α-chymotrypsin (SCLAVO S.p.A.) (9.2 g) was added.

The mixture was left at 25° C. for 4.5 hours under magnetic stirring. The phases were separated and the aqueous phase was extracted with methylene chloride (2×150 ml). The collected organic extracts were evaporated at reduced pressure.

An oil (10 g) was obtained which at the HPLC analysis (Chiracell OD column, 250 mm, internal diameter 4.6 mm, 10 μm, Daicel Chemical Industries Ltd.) showed to be constituted by methyl ester of trans-3-(4-methoxyphenyl)-glycidic acid (4.8 g) with an enantiomeric ratio (2R,3S):(2S, 3R)=30:70 and by butyl ester of trans-3-(4-methoxyphenyl)-glycidic acid (4.44 g) with an enantiomeric ratio (2R, 3S):(2S,3R)=77:23.

The mixture of the methyl and butyl ester was separated by chromatography on silica gel (eluent hexane:ethyl acetate=7:3).

Methyl ester of trans-3-(4-methoxyphenyl)-glycidic acid (4.7 g) with an enantiomeric ratio (2R,3S):(2S,3R)=30:70 and butyl ester of trans-3-(4-methoxyphenyl)-glycidic acid (4.03 g) with an enantiomeric ratio (2R,3S):(2S,3R)=78:22 were thus obtained.

What we claim is:

1. A process for the preparation of esters of (2R,3S)-3-(4-methoxyphenyl)-glycidic acid of the formula

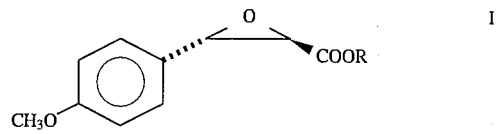

wherein R is a linear or branched $C_1$–$C_8$ alkyl group; a $C_5$–$C_6$ cycloaklyl group or a 2,2-dimethyl-1,3-dioxolane-4-methyl group;
which consists of:

subjecting an enantiomeric mixture of (2R,3S)-3-(4-methoxyphenyl)-glycidic acid methyl ester or ethyl ester (I, R=$CH_3$, $C_2H_5$) and its (2S,3R)-enantiomer (ent-I) to an enantioselective enzymatic transesterification, in the presence of a lipase of animal or microbial origin as the enzyme and in the presence of an alcohol which is different from the alcohol esterifying compound I and ent-I and which is selected from the group consisting of a linear or branched $C_2$–$C_8$ aliphatic alcohol, a $C_5$–$C_6$ cycloaliphatic alcohol and 2,2-dimethyl-1,3-dioxolane-4-methanol, optionally in the presence of a suitable solvent or mixture of solvents; and separating the transesterified ester from the untransesterified ester.

2. The process according to claim 1 wherein the alcohol used for the enantioselective enzymatic transesterification is selected from the group consisting of ethanol, n-propanol, 2-propanol, n-butanol, 2-butanol, 2-methyl-2-propanol, n-pentanol, 2-pentanol, 3-pentanol, n-hexanol, n-heptanol, 2-haptanol, n-octanol, 2-octanol, cyclohexanol, cyclopentanol, and 2,2-dimethyl-1,3-dioxolane-4-methanol.

3. The process according to claim 2 wherein the alcohol used for the enantioselective enzymatic transesterification is selected from the group consisting of n-butanol, 2-butanol, cyclohexanol, n-octanol and 2,2-dimethyl-1,3-dioxolane-4-methanol.

4. The process according to claim 1 wherein the enantioselective enzymatic transesterification is carried out in the presence of a solvent or of a mixture of solvents selected from the group consisting of hexane, cyclohexane, toluene, benzene, methyl-ethyl-ketone and ethyl ether.

5. The process according to claim 1 wherein the enzyme used for the enantioselective enzymatic transesterification is a lipase of animal origin selected between pig liver and pig pancreas lipase.

6. A process according to claim 1 wherein the enzyme used for the enantioselective enzymatic transesterification is a lipase of microbial origin selected from a microbe of the group consisting of *Candida, Mucor, Pseudomonas* and *Aspergillus*.

7. The process according to claim 6 wherein the enzyme used for the enantioselective enzymatic transesterification is a lipase of microbial origin selected among lipases from *Candida*.

8. The process according to claim 1 wherein the enzyme used for the enantioselective enzymatic transesterification is α-chymotrypsin.

* * * * *